United States Patent
Aoshima et al.

(10) Patent No.: US 6,509,304 B1
(45) Date of Patent: Jan. 21, 2003

(54) FIBER-CONTAINING DETERGENT COMPOSITION

(75) Inventors: Masayoshi Aoshima, Tokyo (JP); Toshiya Ono, Tokyo (JP); Atsushi Tomokuni, Tokyo (JP); Hiroko Tsuda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/926,133

(22) PCT Filed: Jan. 19, 2001

(86) PCT No.: PCT/JP01/00340

§ 371 (c)(1),
(2), (4) Date: Sep. 7, 2001

(87) PCT Pub. No.: WO01/52798

PCT Pub. Date: Jul. 26, 2001

(30) Foreign Application Priority Data

Jan. 19, 2000 (JP) ........................................ 2000-010566

(51) Int. Cl.⁷ ................................................ A61K 7/50
(52) U.S. Cl. ...................... 510/130; 510/138; 510/156; 424/70.12; 424/401
(58) Field of Search ................................ 510/130, 136, 510/156, 138; 424/401, 70.1, 70.12

(56) References Cited

U.S. PATENT DOCUMENTS 5,965,146 A * 10/1999 Franzke et al. ............... 424/40

FOREIGN PATENT DOCUMENTS

| JP | 62-39507 | | 2/1987 |
|----|----------|---|--------|
| JP | 62238211 | * | 10/1987 |
| JP | 62-238211 | | 10/1987 |
| JP | 63-238008 | | 10/1988 |
| JP | 3-106809 | | 5/1991 |
| JP | 03106809 | * | 7/1991 |
| JP | 4-124119 | | 4/1992 |
| JP | 7-258020 | | 10/1995 |
| JP | 9-12427 | | 1/1997 |
| JP | 9-20647 | | 1/1997 |
| JP | 10-114634 | | 5/1998 |
| JP | 10-167926 | | 6/1998 |
| JP | 10-287542 | | 10/1998 |

* cited by examiner

*Primary Examiner*—Necholus Ogden
(74) *Attorney, Agent, or Firm*—Oblon, Spivak, McClelland, Maier & Neustadt, PC

(57) ABSTRACT

The invention relates to a detergent composition comprising the following components (A) and (B):

(A) 3 to 60% by weight of at least one surfactant selected from anionic surfactants, amphoteric surfactants and hydrophilic nonionic surfactants; and (B) 0.1 to 50% by weight of fiber having an average fiber length of 0.02 to 1 mm.

The detergent composition has a high detergent effect and excellent massaging ability and rinsability.

20 Claims, No Drawings

FIBER-CONTAINING DETERGENT COMPOSITION

TECHNICAL FIELD

The present invention relates to a detergent composition which gives users a granular feel upon use, permits actually feeling a cleansing effect and has a high detergent effect and excellent mass aging ability and rinsability.

BACKGROUND ART

Many conventional detergent compositions for removing smear or dirt on the skin and makeup have been used by applying them to the skin, cause the smear or dirt to come to the surface of the skin by massaging and rinsing out them with water. However, such detergent compositions have involved such problems that sufficient massaged feeling and detergent effect are not achieved, and they give an actual feeling that the smear and makeup have been removed only to a poor extent. In addition, in such detergent compositions, a nonionic surfactant is generally incorporated, and the compositions have good detergency to oily smear such as makeup, but are not fully satisfactory from the viewpoint of rinsability because they have a feel of sliminess upon rinsing with water.

Further, detergents in which a scrubbing agent composed of any of various kinds of powder is incorporated (Japanese Patent Application Laid-Open Nos. 238008/1988, 124119/1992 and 20647/1997), and peeling or gommage cosmetics in which powder or fiber is incorporated (Japanese Patent Application Laid-Open Nos. 39507/1987, 167926/1998, 287542/1998, 258020/1995 and 12427/1997) have also been known. However, they have been unable to achieve a sufficient detergent effect and give an actual feeling thereof, and have not been fully satisfactory from the viewpoint of massaging ability and rinsability.

It is an object of the present invention to provide a detergent composition which has a high detergent effect, permits actually feeling such an effect and has excellent massaging ability and rinsability.

DISCLOSURE OF THE INVENTION

The present inventors have found that when a specific surfactant and fiber having a specific fiber length are used in combination, a detergent composition which has a high detergent effect, permits actually feeling such an effect because the fiber aggregates upon use to capture smear or dirt therein, and also has excellent massaging ability and rinsability can be provided.

The present invention provides a detergent composition comprising the following components (A) and (B):

(A) 3 to 60% by weight of at least one surfactant selected from anionic surfactants, amphoteric surfactants and hydrophilic nonionic surfactants; and (B) 0.1 to 50% by weight of fiber having an average fiber length of 0.02 to 1 mm.

The present invention also provides a method of cleansing the skin, which comprises using the detergent composition described above. In the present invention, the cleansing of the skin includes both removal of smear or dirt on the skin and removal of makeup.

BEST MODE FOR CARRYING OUT THE INVENTION

The anionic surfactants among the surfactants of the component (A) used in the present invention include those having a hydrophobic group having 12 to 24 carbon atoms, and examples thereof include higher fatty acid salts, N-acylamino acid type surfactants, phosphate ester type surfactants, fatty acid monoglyceride sulfate salts, acylated isethionates, acylated sarcosinates, acylated taurates, N-alkylamidoalkanol sulfate salts, alkylsulfates, alkylbenzenesulfonates, polyoxyalkylene alkyl ether sulfates, polyoxyalkylene alkenyl ether sulfates, polyoxyalkylene alkyl phenyl ether sulfates, alkyl sulfosuccinate salts and α-olefin sulfonates. Among these, higher fatty acid salts, phosphate ester type surfactants and polyoxyalkylene alkyl ether sulfates are particularly preferred.

The amphoteric surfactants include those having a hydrophobic group having 12 to 24 carbon atoms and may be any of carbobetaine type, amidobetaine type, sulfobetaine type, amidosulfobetaine type, imidazolinium betaine type, phosphobetaine type and alkylamine oxide type surfactants, and examples thereof include lauryldimethylaminoacetic acid betaine, myristyldimethylaminoacetic acid betaine, oleyldimethylaminoacetic acid betaine, coco-alkyldimethylaminoacetic acid betaine, lauramide propylbetaine, coconut oil fatty acid amide propylbetaine, palm kernal fatty acid amide propylbetaine, laurylhydroxysulfobetaine, 2-alkyl-N-carboxymethyl-N-hydroxyethylimidazolinium betaine, lauryldimethylamine oxide, myristyldimethylamine oxide, oleyldimethylamine oxide and coco-alkyldimethylamine oxide. Among these, lauryldimethylaminoacetic acid betaine, lauramide propylbetaine, laurylhydroxysulfobetaine, 2-alkyl-N-carboxymethyl-N-hydroxyethylimidazolinium betaine and lauryldimethylamine oxide are particularly preferred.

As the hydrophilic nonionic surfactants, are preferred those having an HLB of at least 9, particularly an HLB of 10 to 17, more particularly an HLB of 12 to 17. The term "HLB" as used herein is an index to hydrophile-lipophile balance. In the present invention, a value calculated out in accordance with the following equation by Oda, Teramura et al. (Oda and Teramura, "Synthesis of Surfactants and Application thereof", p. 501 (Maki Shoten)) is used.

$$HLB = \frac{\sum Organicity\ value}{\sum Inorganicity\ value} \times 10$$

Examples of the hydrophilic nonionic surfactants include polyoxyethylene alkyl ethers, polyoxyethylene alkenyl ethers, polyoxyethylene alkyl phenyl ethers, polyoxyethylene hardened castor oil, polyoxyethylene glycerol fatty acid esters, polyoxyethylene sorbitan fatty acid esters, polyoxyethylene sorbit fatty acid esters, higher fatty acid sucrose esters, glycerol fatty acid esters, glycol fatty acid esters, sorbitan fatty acid esters and alkylglucoside type surfactants. Among these, polyoxyethylene alkyl ethers, polyoxyethylene hardened castor oil, polyoxyethylene glycerol fatty acid esters and polyoxyethylene sorbitan fatty acid esters are particularly preferred.

The surfactants of the component (A) may be used either singly or in any combination thereof and are contained in a proportion of 3 to 60% by weight, preferably 5 to 40% by weight, particularly preferably 5 to 30% by weight based on the total weight of the composition. If the content is lower than 3% by weight, sufficient detergency cannot be achieved, and rinsability of the resulting detergent composition is also deteriorated. On the other hand, any content higher than 60% by weight results in a detergent composition which is poor in spreadability and fittability and deteriorated in massaging ability upon application to the skin.

The fiber of the component (B) is a short fibrous material having a specific fiber length; the average fiber length being 0.02 to 1 mm. The fiber is entangled upon use to form aggregate of the fiber. If the average fiber length is shorter than 0.02 mm, the fiber is hard to be entangled upon use, and so no sufficient detergent effect is achieved. If the average fiber length exceeds 1 mm, the fiber is entangled to an excessive extent, and so the resulting detergent composition cannot give users a moderate granular feel, and a feel upon use becomes poor. In this invention, the average fiber length is a value determined by means of a laser diffraction/scattering type particle size distribution meter (for example, HORIBA LA-910 manufactured by Horiba Ltd.).

The fineness of the fiber is preferably a fifth, particularly a tenth as much as the fiber length.

Examples of a material for the fiber include natural, semisynthetic and synthetic materials such as cellulose, polyester, polyamide and polyacrylonitrile types. More specifically, water-insoluble celluloses such as powdered cellulose, crystalline cellulose, cellulose ethers, cellulose esters, rayon and acetate; wool, silk, nylon, acrylic and polyester are mentioned.

Among these, water-insoluble celluloses are preferred, and examples thereof include commercially available products such as KC Flock (product of Nippon Paper Co., Ltd.) marketed as powdered cellulose. Those obtained by loosening a nonwoven fabric or tissue paper fabricated by intermingling of short fibers, and raw materials for these nonwoven fabric and tissue paper may also be used. In the present invention, the powdered cellulose is composed mainly of cellulose obtained by decomposing pulp (Notification No. 7 of the Ministry of Health and Welfare; Official Document for food additives), and the crystalline cellulose is composed mainly of crystalline cellulose obtained from pulp (Notification No. 7 of the Ministry of Health and Welfare; Official Document for food additives).

The fibers of the component (B) may be used either singly or in any combination thereof and are contained in a proportion of 0.1 to 50% by weight, preferably 0.1 to 30% by weight, particularly preferably 1 to 20% by weight based on the total weight of the composition. If the content is lower than 0.1% by weight, the fiber does not sufficiently aggregate to give a granular feel, and so the granular feel cannot be given. On the other hand, any content higher than 50% by weight results in a detergent composition which is hard to be spread and deteriorated in massaging ability upon application to the skin. It is desirable that the fiber of the component (B) be dispersed in a substantially non-aggregated state in the detergent composition before use.

(C) A liquid oil may be additionally contained in the detergent composition according to the present invention.

As the liquid oil, is preferred a liquid having flowability at 25° C., and examples thereof include silicone oils such as dimethyl polysiloxane, dimethyl cyclopolysiloxane and methylphenyl polysiloxane; fatty oils such as olive oil, avocado oil, castor oil and macadamia nut oil; hydrocarbons such as liquid paraffin and squalane; dialkyl ethers having a branched alkyl group; higher alcohols such as isostearyl alcohol; esters such as isopropyl myristate, isopropyl palmitate, hexyldecyl isostearate and diisostearyl malate; and besides jojoba oil, liquid lanolin, liquid diglycerides and triglycerides. Among these, silicone oils and dialkyl ethers having a viscosity of at most 50 mPa·s, with those having a viscosity of at most 20 mPa·s being particularly preferred from the viewpoint of enhancing detergency.

These liquid oils may be used either singly or in any combination and are preferably contained in a proportion of 20 to 60% by weight, particularly 30 to 60% by weight based on the total weight of the composition. It is particularly preferred that the liquid oil having a viscosity of at most 20 mPa·s be contained in a proportion of 10 to 50% by weight.

When (C) the liquid oil is used, a surfactant having a branched hydrophobic group such as an octyldodecyl group is preferred as the surfactant of the component (A) in that it is high in emulsifying power, and so a great amount of the liquid oil is easy to be stably incorporated.

When (C) the liquid oil is used, it is also preferred that fiber having an average fiber length of 0.1 to 1 mm be used as the component (B).

(D) A water-soluble cellulose may be additionally contained in the detergent composition according to the present invention. In the composition according to the present invention containing (D) the water-soluble cellulose, the water-soluble cellulose is deposited when a certain amount of water is added to the composition upon use. The water-soluble cellulose deposited grows as aggregate particles while entangling the dispersed fiber therein. Therefore, aggregate is easily formed even when the fiber length of the component (B) is very short. The water-soluble cellulose is dissolved again in a great excess of water to easily disperse the aggregate. Therefore, even if the aggregate is put into an eye, it is immediately washed out with water. Accordingly, the water-soluble cellulose-containing composition according to the present invention is higher in safety.

When (D) the water-soluble cellulose is contained, it is preferred that the average fiber length of the component (B) be generally 0.02 to 0.1 mm. However, when other components in the composition deteriorate the easy agglomeration of the fiber or lower the hardness of the aggregate, longer fiber may be preferably used.

As (D) the water-soluble cellulose used, is preferred hydroxyalkyl cellulose, particularly hydroxypropyl cellulose. These water-soluble celluloses may be used either singly or in any combination thereof and are preferably contained in a proportion of 0.01 to 10% by weight, particularly 0.05 to 8% by weight, more particularly 0.1 to 5% by weight based on the total weight of the composition.

As the mechanism that the water-soluble cellulose is deposited when water is added to the composition according to the present invention containing (D) the water-soluble cellulose, the following two mechanisms can be given. First, the water-soluble cellulose dissolved in concentrated aqueous polyhydric alcohol (particularly, aqueous polyethylene glycol) having a ratio of polyhydric alcohol to water of, for example, about 80:20 is deposited when the concentration of water is increased to change the above ratio to an extent exceeding 70:30, since the solubility of the water-soluble cellulose in the aqueous polyhydric alcohol is lowered. Second, a salt in a crystalline state is dissolved in water to form a solution containing the salt at a high concentration, and then the water-soluble cellulose is deposited by salting out. Accordingly, it is preferred that (E) a polyhydric alcohol and/or (G) a salt be additionally contained in the composition according to the present invention.

Examples of (E) the polyhydric alcohol include polyethylene glycol, 1,3-butylene glycol, isoprene glycol and propylene glycol. Among these, polyethylene glycol, specifically, polyethylene glycol having an average molecular weight of 100 to 4,000, particularly 100 to 2,000, more particularly 200 to 1,000 is preferred.

These (E) polyhydric alcohols may be used either singly or in any combination thereof and are preferably contained in a proportion of 0.5 to 85% by weight, particularly 1 to 80% by weight, more particularly 5 to 75% by weight based on the total weight of the composition. At this time, (F) water is preferably contained in a proportion of 0 to 35% by weight, particularly 0.5 to 30% by weight, more particularly 1 to 25% by weight. A weight ratio of (E) to (F) is preferably controlled to 100:0 to 70:30, particularly 100:0 to 75:25, more particularly 95:5 to 80:20.

Examples of (G) the salt include chlorides, sulfates, phosphates, citrates, tartarates and acetates, and salts whose anion or cation is a polyvalent ion are preferred because the salting-out effect is high.

These salts are preferably contained in a proportion of 0.1 to 30% by weight, particularly 0.5 to 25% by weight, more particularly 1 to 20% by weight based on the total weight of the composition.

In the detergent compositions according to the present invention, components used in the conventional detergent compositions, for example, other surfactants than the above-described surfactants, anionic polymers, nonionic polymers, cationic polymers, alcohols, other oily components than the above-described liquid oils, other powders than the above-described fibers, moisturizers, plant extracts, ultraviolet absorbents, germicides, anti-inflammatory agents, inorganic salts, pearlescent agents, metal chelating agents, antioxidants, preservatives, pH adjustors, colorants, perfume bases, etc., may be suitably incorporated in addition to the above-described components.

The detergent compositions according to the present invention can be prepared in accordance with a method known per se in the art. No particular limitation is imposed on the form thereof, and the compositions may be formulated in any forms such as liquid, paste, cream, solid and powder. It is particularly preferred that the detergent compositions be prepared into forms of liquid, paste and cream.

The detergent compositions according to the present invention are preferably provided as skin detergent compositions such as facial soap, makeup removers and body shampoos, and particularly suitable for use as facial soap and cleansing compositions. However, the compositions may also be applied to other uses and provided as, for example, detergent compositions for hard surfaces. When the composition is provided as, particularly, a skin detergent composition for removing makeup, a preferred embodiment is such that the hydrophilic nonionic surfactant among the surfactants of the component (A) is used as a surfactant in a primary amount, and the liquid oil mentioned as the component (C) or the water-soluble cellulose mentioned as the component (D) is used in combination therewith. With respect to the surfactants, the primary amount means that the amount is at least 80% by weight, preferably at least 90% by weight based on the total weight of the surfactants.

In the detergent compositions according to the present invention, particularly, the skin detergent compositions, it is desirable that all the components thereof be compatible with the skin of at least a healthy person upon application to the skin, i.e., do not cause unpleasant irritation, inflammation and/or allergic response.

The cleansing of the skin with the detergent composition according to the present invention is conducted by applying the detergent composition according to the present invention to the skin, massaging the skin portion, to which the detergent composition has been applied, to aggregate the fiber and then rinsing the detergent composition containing the aggregated fiber out of the skin with water. Since the conventional gommage cosmetics scarcely contain any surfactant, the whole composition is scrubbed out of the skin in a form like eraser refuse. On the other hand, when the composition according to the present invention is used, a surfactant-containing fluid portion in the form of liquid, cream or paste is left in a state that the fiber has aggregated. Therefore, this portion is rinsed out together with the aggregated fiber from the skin upon the use. Accordingly, a high detergent effect is achieved.

The detergent composition according to the present invention has no granular feel before use. However, the composition is applied to the skin upon use, and the skin is massaged, whereby the fiber is aggregated, and the granular feel is brought about herewith to achieve an excellent massaging effect. In addition, smear or dirt and/or makeup is captured in the aggregated fiber, thereby achieving a high detergent effect and moreover permitting actually feeling the removal of the smear and/or makeup by the granular feel brought about by the aggregation. Accordingly, good cleansability is exhibited without incorporating any scrubbing agent.

EXAMPLES

Examples 1 to 10

Detergent compositions having their corresponding formulations shown in Tables 1 and 2 were prepared in accordance with a method known per se in the art to evaluate them as to detergent effect, granular feel, actual feeling, massaging ability and rinsability. The results are shown collectively in Tables 1 and 2.

(Evaluation Methods)

(1) Detergent Effect:

A commercially available lipstick was applied on to the inside of the forearm in the size (about 0.05 g) of a circle having a diameter of 2 cm, and each (0.1 g) of the detergent compositions was applied thereto to massage the applied portion 40 times (the number of times of massaging was determined to be once at the time the composition was intimately mixed once with the lipstick applied in such a manner that a circle is drown with an index finger). The removal of the lipstick after the composition was rinsed out with water was visually observed to evaluate the composition as to the detergent effect in accordance with the following standard:

○: Little lipstick was left;

Δ: About a half of the lipstick was left;

X: Most of the lipstick was left.

(2) Granular Feel:

A commercially available foundation (about 0.01 g) was applied on to a 4 cm×7 cm portion on the inside of the forearm, and each (0.07 g) of the detergent compositions was applied thereto to massage the applied portion (the number of times of massaging was determined to be once at the time an index finger was reciprocatingly moved once on the applied portion). The composition was evaluated as to the granular feel by the number of times of massaging, at which the granular feel by the fiber (to feel the formation of aggregate of the fiber on the skin) was brought about, in accordance with the following standard:

○: Fully felt (less than 40 times);

Δ: Felt (not less than 40 times, but less than 80 times);

X: Not felt (not less than 80 times).

(3) Actual Feeling:

Ten women panelists evaluated each of the detergent compositions as to the actual feeling on the detergent effect (effect to remove smear of makeup such as foundation, lipstick or eye makeup) upon its use and ranked in accordance with the following standard:

○: At least 6 panelists judged to be actually felt;
Δ: Three to five panelists judged to be actually felt;
X: At most 2 panelists judged to be actually felt.

(4) Massaging Ability and Rinsability:

Ten women panelists organoleptically evaluated each of the detergent compositions as to the massaging ability (to permit giving a feeling that the composition has moderate viscosity and resistance, and is easy to be spread overall the face and intimately mixed with smear of makeup) upon its use and rinsability (to rinse the detergent composition out of the skin by smaller times of rinsing) and ranked in accordance with the following standard:

○: At least 6 panelists judged to be good;
Δ: Three to five panelists judged to be good;
X: At most 2 panelists judged to be good.

TABLE 1

| | Example (% by weight) | | | | | | |
|---|---|---|---|---|---|---|---|
| | 1 | 2 | 3 | 4 | 5 | 6 | 7 |
| Polyoxyethylene octyl dodecyl ether (25 EO) (HLB = 14) | 10 | 15 | | | | 10 | 10 |
| Polyoxyethylene octyl dodecyl ether (20 EO) (HLB = 13) | | | 8 | 10 | 12 | 5 | 5 |
| Polyoxyethylene hardened castor oil (40 EO) (HLB = 13) | | | | | | | |
| Polyoxyethylene sorbitan isostearate (20 EO) (HLB = 13) | | | | | | | |
| Sorbitan sesquioleate (HLB = 5) | | | | | | | |
| Monoglyceryl stearate | | | | | | | |
| Isostearyl glyceryl ether | | 1 | 1 | 1 | | | |
| 2-Hexyldecyl phosphate arginine | 0.1 | 0.1 | | 0.1 | 0.1 | 0.1 | 0.1 |
| Lauryldimethylamine oxide (33% aqueous solution) | 0.6 | 0.6 | 0.6 | 0.6 | 0.6 | 0.6 | 0.6 |
| Powdered cellulose (average length: 0.1 mm) | 8 | | | 10 | | 8 | 8 |
| Powdered cellulose (average length: 0.5 mm) | | 5 | | | 4 | | |
| Powdered cellulose (average length: 1.0 mm) | | | 2 | | | | |
| Rayon fiber (average length: 0.5 mm) | | | | 5 | 2 | | |
| Rayon fiber (average length: 1.0 mm) | | | | | | | |
| Liquid paraffin*1 | 10 | 10 | 10 | 10 | 10 | 10 | 10 |
| Squalane*2 | | | | | | | |
| Dimethyl cyclopolysiloxane*3 | 5 | 10 | 8 | 10 | 9 | 5 | 5 |
| Cetyl-1,3-dimethyl butyl ether*4 | 5 | 10 | 15 | 10 | 10 | 5 | 5 |
| Isopropyl myristate*5 | | | | | | | |
| 2-Ethylhexanoic acid triglyceride*6 | 10 | 10 | 10 | 10 | 10 | 10 | 10 |
| Glyceryl tri(caprylate·caprate)*7 | | 5 | | 5 | | | |
| Cetanol | | | | | | | |
| Microcrystalline wax | | | | | | | |
| Polyoxyethylene methylglycoside (10 EO) | 14 | 10 | 15 | 7 | 8 | 10 | |
| Polyoxyethylene methylglycoside (20 EO) | | | | | | | 4 |
| Polyethylene glycol 400 | | | | | | | 14 |
| Glycerol | 3 | 3 | 3 | 2 | 3 | 3 | 3 |
| Sorbitol | 12 | 10 | 15 | 4 | 15 | 12 | 12 |
| Ethanol | | | 1 | | 0.5 | | |
| 1,3-Butylene glycol | | 0.5 | 1 | | 0.5 | | |
| Dipropylene glycol | | | | | 0.5 | | |
| Water | 22.3 | 9.8 | 10.4 | 10.3 | 14.8 | 17.3 | 17.3 |
| Removal of smear or dirt | ○ | ○ | ○ | ○ | ○ | ○ | ○ |
| Granular feel | ○ | ○ | ○ | ○ | ○ | ○ | ○ |
| Actual feeling that smear or dirt has been removed by granules | ○ | ○ | ○ | ○ | ○ | ○ | ○ |
| Massaging ability | ○ | ○ | ○ | ○ | ○ | ○ | ○ |
| Rinsability | ○ | ○ | ○ | ○ | ○ | ○ | ○ |

Viscosity at 25° C. (mPa·s):
*1 = 18,
*2 = 30,
*3 = 2.2,
*4 = 7.3,
*5 = 4.7,
*6 = 32,
*7 = 26.

TABLE 2

| | Example (% by weight) | | | Comparative Example | | | |
|---|---|---|---|---|---|---|---|
| | 8 | 9 | 10 | 1 | 2 | 3 | 4 |
| Polyoxyethylene octyl dodecyl ether (25 EO) (HLB = 14) | 10 | 10 | | | | | |
| Polyoxyethylene octyl dodecyl ether (20 EO) (HLB = 13) | 5 | | | | 12 | | |
| Polyoxyethylene hardened castor oil (40 EO) (HLB = 13) | | 5 | | | | | 0.5 |
| Polyoxyethylene sorbitan isostearate (20 EO) (HLB = 13) | | | 18 | | | 2.8 | |
| Sorbitan sesquioleate (HLB = 5) | | | | 10 | | | |
| Monoglyceryl stearate | | | | | | 2.2 | |
| Isostearyl glyceryl ether | | | | 1 | | | 1 |
| 2-Hexyldecyl phosphate arginine | 0.1 | 0.1 | 0.1 | 0.1 | 0.1 | | 0.1 |
| Lauryldimethylamine oxide (33% aqueous solution) | 0.6 | 0.6 | 0.6 | 0.6 | 0.6 | | 0.6 |
| Powdered cellulose (average length: 0.1 mm) | 8 | 8 | | | | | |
| Powdered cellulose (average length: 0.5 mm) | | | 10 | 4 | 0.05 | 4 | 5 |
| Powdered cellulose (average length: 1.0 mm) | | | | | | | |
| Rayon fiber (average length: 0.5 mm) | | | | | 2 | | 2 |
| Rayon fiber (average length: 1.0 mm) | | | | 1 | | | |
| Liquid paraffin*1 | 10 | 10 | 10 | 10 | 10 | | 10 |
| Squalane*2 | | | | | | 15 | |
| Dimethyl | 30 | 5 | 9 | 5 | 9 | | 10 |

TABLE 2-continued

|  | Example | | | Comparative Example | | | | (% by weight) |
| --- | --- | --- | --- | --- | --- | --- | --- | --- |
|  | 8 | 9 | 10 | 1 | 2 | 3 | 4 | |
| cyclopolysiloxane*3 | | | | | | | | |
| Cetyl-1,3-dimethyl butyl ether*4 | 5 | 5 | 10 | 5 | 10 | | 10 | |
| Isopropyl myristate*5 | | | | | | 8 | | |
| 2-Ethylhexanoic acid triglyceride*6 | 10 | 10 | 10 | 10 | 10 | | 10 | |
| Glyceryl tri(caprylate · caprate)*7 | | | | 5 | | | 5 | |
| Cetanol | | | | | | 4 | | |
| Microcrystalline wax | | | | | | 10 | | |
| Polyoxyethylene methylglycoside (10 EO) | 5 | 10 | 10 | 18 | 15 | | | |
| Polyoxyethylene methylglycoside (20 EO) | | 4 | | | | | | |
| Polyethylene glycol 400 | | | | | | | | |
| Glycerol | 3 | 3 | 5 | 3 | 3 | 10 | | |
| Sorbitol | 5 | 12 | 10 | 27 | 20 | | | |
| Ethanol | | | | | | | | |
| 1,3-Butylene glycol | | | | | | | | |
| Dipropylene glycol | | | | | | 5 | | |
| Water | 8.3 | 17.3 | 5.3 | 5.3 | 10.25 | 37 | 47.8 | |
| Removal of smear or dirt | ○ | ○ | ○ | x | ○ | x | x | |
| Granular feel | ○ | ○ | ○ | ○ | x | ○ | ○ | |
| Actual feeling that smear or dirt has been removed by granules | ○ | ○ | ○ | ○ | x | Δ | ○ | |
| Massaging ability | ○ | ○ | ○ | ○ | ○ | Δ | x | |
| Rinsability | ○ | ○ | ○ | x | ○ | x | x | |

Viscosity at 25° C. (mPa · s):
*1= 18,
*2= 30,
*3= 2.2,
*4= 7.3,
*5= 4.7,
*6= 32,
*7= 26.

As apparent from the results shown in Tables 1 and 2, all the invention products (all, uniform paste at the time the compositions had been prepared) gave users a granular feel upon use, had excellent massaging ability and a high detergent effect, permitted actually feeling the effect and also had good rinsability. On the other hand, Comparative Example 1 was poor in detergent effect and rinsability because the surfactant was low in HLB and not hydrophilic. Comparative Example 2 gave neither granular feel nor actual feeling because the amount of the fiber was little. Comparative Example 3 became like eraser refuse as a whole upon use and was hence insufficient in actual feeling and massaging ability because the composition contained solid oils (cetanol and microcrystalline wax), and moreover was poor in detergent effect and rinsability because the amount of the surfactant was little. Comparative Example 4 became separated into 2 phases at the time the composition had been prepared and was poor in massaging ability because the amount of the surfactant was little. In addition, the detergent effect and rinsability were poor.

Detergent compositions having their corresponding formulations shown in Table 3 were prepared in accordance with a method known per se in the art to evaluate them as to detergent effect, granular feel, actual feeling, massaging ability, rinsability and remaining tendency. The results are shown collectively in Table 3.

(Evaluation Methods)

(1) Detergent Effect:

Each of the detergent compositions was tested in the same manner as in Examples 1 to 10 to visually observe the removal of the lipstick after the composition was rinsed out with water, thereby evaluating the composition as to the detergent effect in accordance with the following standard:

A: Little lipstick was left;

B: A little or about 30% of the lipstick was left;

C: About a half of the lipstick was left;

D: Most of the lipstick was left.

(2) Granular Feel:

Ten panelists evaluated each of the detergent compositions as to the granular feel brought about by the fiber when the smear of makeup was removed with the detergent composition and ranked in accordance with the following standard:

A: At least 9 panelists judged to be actually felt;

B: At least 7 panelists judged to be actually felt;

C: At least 5 panelists judged to be actually felt;

D: At most 4 panelists judged to be actually felt.

(3) Evaluation of Actual Feeling Upon Cleansing:

Ten panelists evaluated each of the detergent compositions as to the actual feeling on the detergent effect when smear of makeup was removed with the detergent composition in the same manner as in Examples 1 to 10 and ranked in accordance with the following standard:

A: At least 9 panelists judged to be actually felt;

B: At least 7 panelists judged to be actually felt;

C: At least 5 panelists judged to be actually felt;

D: At most 4 panelists judged to be actually felt.

(4) Evaluation of Massaging Ability and Rinsability:

Ten panelists organoleptically evaluated each of the detergent compositions as to the massaging ability and rinsability when smear of makeup was removed with the detergent composition in the same manner as in Examples 1 to 10 and ranked in accordance with the following standard:

A: At least 9 panelists judged to be good;

B: At least 7 panelists judged to be good;

C: At least 5 panelists judged to be good;

D: At most 4 panelists judged to be good.

(5) Evaluation of Remaining Tendency:

Ten panelists organoleptically evaluated each of the detergent compositions as to a remaining feeling (a feeling that a film was formed on the skin fully rinsed and toweled) when smear of makeup was removed with the detergent composition and ranked in accordance with the following standard:

A: At least 9 panelists judged to give no remaining feeling;

B: At least 7 panelists judged to give no remaining feeling;

C: At least 5 panelists judged to give no remaining feeling;

D: At most 4 panelists judged to give no remaining feeling.

TABLE 3

|  | Example |  |  |  |  |  |  |
| --- | --- | --- | --- | --- | --- | --- | --- |
|  | 11 | 12 | 13 | 14 | 15 | 16 | 17 |
| Polyoxyethylene glycol monolaurate (Emanon 1112*¹, Kao) | 15 |  |  | 15 | 15 | 15 | 15 |
| Polyglyceryl monolaurate (Sunsoft M-12J*², Taiyo Kagaku) |  | 15 |  |  |  |  |  |
| Potassium lauryl phosphate (crystalline powder) (neutralization salt of MAP-20H, Kao) |  |  | 3 |  |  |  |  |
| Potassium laurate (crystalline powder) (neutralization salt of Lunac L-98, Kao) |  |  | 8 |  |  |  |  |
| Potassium myristate (crystalline powder) (neutralization salt of Parmac 98-14, Kao) |  |  | 3 |  |  |  |  |
| Hydroxypropyl cellulose (HPC-H*⁵, Nippon Soda) | 1 | 1 | 1 |  | 1 | 1 | 1 |
| Hydroxypropyl cellulose (HPC-M*⁶, Nippon Soda) |  |  |  | 1 |  |  |  |
| Powdered cellulose (KC Flock W-400G*³, Nippon Paper) | 10 | 10 | 10 | 10 |  | 10 | 10 |
| Crystalline cellulose (Avicel PH101*⁴, Asahi Chemical Industry) |  |  |  |  | 10 |  |  |
| Polyethylene glycol 400 (PEG-400, Sun Chemical) | 49 | 49 | 50 | 49 | 49 | 39 | 39 |
| Polyethylene glycol 200 (PEG-200, Sun Chemical) | 15 | 15 | 15 | 15 | 15 | 15 | 15 |
| Purified water | 10 | 10 | 10 | 10 | 10 | 10 | 10 |
| Magnesium sulfate |  |  |  |  |  | 10 |  |
| Trisodium citrate |  |  |  |  |  |  | 10 |
| Total | 100 | 100 | 100 | 100 | 100 | 100 | 100 |
| Detergent effect | A | A | A | A | A | A | A |
| granular feel | B | C | C | C | C | A | A |
| Actual feeling upon cleansing | B | C | C | B | B | A | A |
| Massaging ability | B | C | C | C | B | A | A |
| Rinsability | B | B | B | A | B | A | A |
| Remaining tendency | B | A | A | B | B | B | B |

*¹Polymerization degree of the ethylene glycol group: 10 (theoretical value), HLB: 13.2;
*²Polymerization degree of the glyceryl group: 10 (theoretical value), HLB: about 15;
*³Particle size: at least 90% of −400 mesh powder (average length: 30 to 40 µm);
*⁴Average particle diameter: 40 µm;
*⁵Substitution degree of the hydroxypropyl group: 53.4 to 77.5%, viscosity (2% aqueous solution, by Brookfield viscometer at 20° C.): 1000 to 4000 (mPa · s);
*⁶Substitution degree of the hydroxypropyl group: 53.4 to 77.5%, viscosity (2% aqueous solution, by Brookfield viscometer at 20° C.): 150 to 400 (mPa · s).

Example 18

A facial soap having the following formulation was prepared in accordance with a method known per se in the art.

The resultant facial soap gave users a granular feel upon use, had a high detergent effect, permitted actually feeling the effect and also had excellent massaging ability and rinsability.

| (Component) | % by weight) |
| --- | --- |
| Myristic acid | 4.0 |
| Lauric acid | 1.0 |
| Potassium hydroxide solution (48%) | 2.58 |
| Lauramide propylbetaine solution (30%) | 20.0 |
| Polyoxyethylene tridecyl ether (HLB = 14) | 1.0 |
| Powdered cellulose (average fiber length: 0.1 mm, KC Flock W-50, product of Nippon Paper Co., Ltd.) | 10.0 |
| Talc | 2.0 |
| Perfume base | 0.01 |
| Purified water | Balance |

INDUSTRIAL APPLICABILITY

The detergent compositions according to the present invention have a high detergent effect, give users a granular feel upon use, permit actually feeling the detergent effect and also have excellent massaging ability and rinsability.

What is claimed is:

1. A detergent composition comprising the following components (A), (B) and (C):

(A) 3 to 60% by weight of at least one surfactant selected from anionic surfactants, amphoteric surfactants and hydrophilic nonionic surfactants;

(B) 0.1 to 50% by weight of fiber having an average fiber length of 0.02 to 1 mm; and (C) 20 to 60% by weight of a liquid oil.

2. The detergent composition according to claim 1, wherein the fiber of the component (B) is a water-insoluble cellulose.

3. The detergent composition according to claim 1, which further comprises (D) 0.01 to 10% by weight of a water-soluble cellulose.

4. The detergent composition according to claim 3, which further comprises (E) 0.5 to 85% by weight of a polyhydric alcohol and (F) 0 to 35% by weight of water and wherein a weight ratio of (E) to (F) is 100:0 to 70:30.

5. The detergent composition according to claim 4, wherein the water-soluble cellulose of the component (D) is hydroxypropyl cellulose, and the polyhydric alcohol of the component (E) is polyethylene glycol.

6. The detergent composition according to claim 3, which further comprises (G) 0.1 to 30% by weight of a salt.

7. The detergent composition according to claim 6, wherein the salt of the component (G) is selected from chlorides, sulfates, phosphates, citrates, tartarates and acetates.

8. The detergent composition according to claim 1, which is a makeup remover.

9. A method of cleansing the skin, which comprises applying the detergent composition according to claim 1 to the skin, massaging the skin portion, to which the detergent composition has been applied, to aggregate the fiber, and rinsing the detergent composition containing the aggregated fiber out of the skin with water.

10. The detergent composition according to claim 1, wherein the liquid oil has flowability at 25° C.

11. The detergent composition according to claim 10, wherein the liquid oil is selected from the group consisting of silicone oils, fatty oils, hydrocarbons, dialkyl ethers, higher alcohols, esters, jojaba oil, liquid lanolin, liquid diglycerides and triglycerides.

12. The detergent composition according to claim 11, wherein the liquid oil is selected from the group consisting of silicone oils and dialkyl ethers having a viscosity of at most 50 mpa·s.

13. The detergent composition according to claim 12, wherein the liquid oil has a viscosity of at most 20 mPa·s.

14. The detergent composition according to claim 1, wherein the surfactant has a branched hydrophobic group.

15. The detergent composition according to claim 1, wherein the fiber has an average fiber length of 0.1 to 1 mm.

16. The detergent composition according to claim 1, wherein component (A) comprises at least an anionic surfactant.

17. The detergent composition according to claim 1, wherein component (A) comprises at least an amphoteric surfactant.

18. The detergent composition according to claim 1, wherein component (A) comprises at least a hydrophilic nonionic surfactant.

19. The detergent composition according to claim 1, wherein the fiber has a ratio of diameter to length of not greater than one fifth.

20. The detergent composition according to claim 19, wherein the fiber has a ratio of diameter to length of not greater than one tenth.

* * * * *